United States Patent
Smith et al.

(10) Patent No.: US 6,742,404 B2
(45) Date of Patent: Jun. 1, 2004

(54) HYBRID PASSIVE/AUTOMATED FLOW PROPORTIONAL FLUID SAMPLER

(76) Inventors: Damien J. Smith, 4033 Riviera Dr., Apartment C, San Diego, CA (US) 92109; Joseph A. Rainwater, 2823 Old Niles Ferry Rd., Maryville, TN (US) 37803; Jan Boll, 304 N. Van Buren St., Moscow, ID (US) 83843

( * ) Notice: Subject to any disclaimer, the term of this patent is extended or adjusted under 35 U.S.C. 154(b) by 0 days.

(21) Appl. No.: 09/826,264

(22) Filed: Apr. 4, 2001

(65) Prior Publication Data

US 2001/0037693 A1 Nov. 8, 2001

Related U.S. Application Data (60) Provisional application No. 60/194,964, filed on Apr. 5, 2000.

(51) Int. Cl.[7] .............................. G01N 1/14; G01N 1/20
(52) U.S. Cl. ................................... 73/863.03; 73/864.34
(58) Field of Search ...................... 73/863.03, 863.33, 73/863.34, 864.34, 863.02, 863.51

(56) References Cited

U.S. PATENT DOCUMENTS

| | | | | |
|---|---|---|---|---|
| 2,272,313 A | * | 2/1942 | Waters ..................... | 73/863.02 |
| 2,729,105 A | * | 1/1956 | McFarland et al. ........... | 73/422 |
| 3,466,782 A | * | 9/1969 | Stuart, Jr. ........................ | 43/4 |
| 3,507,156 A | * | 4/1970 | Merrill, Jr. ................... | 73/423 |
| 3,546,945 A | * | 12/1970 | Collins ........................ | 73/422 |
| 4,022,059 A | | 5/1977 | Schontzler | |
| 4,091,675 A | | 5/1978 | Jennison | |
| 4,151,086 A | | 4/1979 | Frosch | |
| 4,170,798 A | * | 10/1979 | Krumdieck .................... | 4/319 |
| 4,295,801 A | | 10/1981 | Bennett | |
| 4,415,011 A | | 11/1983 | Grant | |
| 4,708,585 A | | 11/1987 | Fukazawa | |
| 4,902,209 A | | 2/1990 | Olson | |
| 5,091,863 A | | 2/1992 | Hungerford | |
| 5,101,670 A | | 4/1992 | Steger | |
| 5,125,801 A | | 6/1992 | Nabity et al. | |
| 5,172,332 A | | 12/1992 | Hungerford | |
| 5,299,141 A | | 3/1994 | Hungerford | |
| 5,413,002 A | * | 5/1995 | Jiskoot et al. ........... | 73/863.03 |
| 5,437,201 A | | 8/1995 | Krueger | |
| 5,441,071 A | | 8/1995 | Doherty | |
| 5,693,894 A | * | 12/1997 | Jobson ..................... | 73/863.03 |
| RE35,824 E | | 6/1998 | Welker | |
| 5,783,758 A | | 7/1998 | Dudley | |
| 6,200,819 B1 | * | 3/2001 | Harvey et al. .............. | 436/179 |

OTHER PUBLICATIONS

The American Heritage® Dictionary of the English Language, Third Edition copyright © 1992 by Houghton Mifflin Company. Electronic version licensed from INSO Corporation; further reproduction and distribution restricted in accordance with the Copyright Law.*

* cited by examiner

*Primary Examiner*—Hezron Williams
*Assistant Examiner*—Charles D. Garber (57) ABSTRACT

The invention discloses a flow proportional fluid sampler. A turbine pump unit has a pump that is powered by the fluid flow of the test site, such as a stream, thereby eliminating the need for outside power for the pump and proportioning the volume of sample taken to the flow velocity. The invention also incorporates a simple pulse counter that monitor's the revolutions of the turbine propeller and can be used to measure velocity. The invention also provides a collection and distribution unit that can collect and store numerous samples in a small, light-weight container.

6 Claims, 9 Drawing Sheets

HYBRID PASSIVE/AUTOMATED FLOW PROPORTIONAL FLUID SAMPLER

RELATED APPLICATIONS

This application follows from Provisional Application Ser. No. 60/194,964, filed on Apr. 5, 2000.

BACKGROUND OF THE INVENTION

1. Field of the Invention

The present invention relates to devices for obtaining samples from moving fluids, such as rivers, streams, pipes, sewers, or irrigation canals.

Water sampling is essential to proper development and management of water and land resources. The need for a clear understanding of the effects of hydro-geomorphologic processes has become increasingly important. Processes such as erosion and fluvial transport of sediment and other associated constituents ("loads"), require accurate measurement of sediment and constituent content within bodies of water. Stream flow and constituent loads are the most important data collected for such an analysis and require flow measurements and water quality sample collection for determining representative concentrations of the constituents of interest. Some of the constituents of interest are suspended solids, phosphorous, nitrogen, and heavy metals. But, natural environmental factors such as geology, soils, climate, runoff, topography, drainage area, and ground cover make obtaining samples and data challenging. For example, in remote forests areas it has become important to monitor runoff to streams and rivers to determine the effects of logging, but obtaining reliable test samples is difficult.

Current monitoring of the hydro-geomorphic processes in stream locations is conducted either by "grab sampling" or by automated samplers. Manual grab samples, which usually provide accurate samples and flow measurements, have the disadvantages of requiring frequent trips to the test site and providing no guarantee of sampling during a runoff event. Current automated devices are versatile in that they are capable of sampling on a programmable time basis or a proportional stream flow basis, and therefore are able to sample during runoff events. Some of the major disadvantages of automated samplers are that they are expensive, use substantial power and require frequent battery charging or expensive and complicated alternative power supplies. Owing to the need to re-charge batteries, automated samplers require frequent attention, which is difficult to provide in remote locations. Moreover, owing to the automated samplers' expense and complexity, users are reluctant to leave them unattended in remote locations, for fear they will be stolen or vandalized. Consequently, there is a need for a simple, inexpensive, flow-proportional sampler that can obtain accurate samples.

To obtain samples and data, and to test and monitor moving fluids, such as streams, there is a need for a sampler that can take adjustable volume samples or samples based on volume or flow-based settings, and that can collect composite or discrete samples. To obtain useful samples, it is critical that samples taken at different times be comparable. For example, in sampling a moving stream over the course of several weeks or seasons, the samples must be taken in proportion to the speed of the stream, which will fluctuate, in order to compare concentrations of sediments or contaminants during dry and wet periods. Without such proportional sampling, samples taken at different times under different stream flow speeds will not be comparable. Thus, flow proportional sampling results in few samples taken during low-flow ("baseflow") conditions and many samples during stormy conditions. This flow proportional sampling provides an accurate hydrograph which can be used to correlate constituent loads in relation to stream flow.

The present invention provides a flow proportional fluid sampler that pumps out a sample at a rate directly related to the flow speed. By linking pump speed to flow speed, samples taken during different fluid flow speeds are comparable. To accomplish this, a propeller or turbine is placed in the fluid to be sampled. The flow of the fluid drives the turbine. A pump is driven mechanically by the turbine. The pump draws a sample from the fluid and pumps it to a sample container. Since the turbine powers the pump, this system does not require an external power source to drive the pump. Since the pumping rate is directly related through the turbine to the fluid's speed, there is no need for a separate mechanism to proportion the rate of sample collection to fluid speed. The present invention also provides a very simple electrical sensor to measure the speed of the fluid being tested, which may be recorded as part of the sample data. The present invention also provides a sample collection system to distribute and store samples taken at different times.

2. Discussion of the Prior Art

Sediment studies require frequent collection of suspended sediment at a test site. Site location, flow conditions, frequency of collection, and operational costs frequently make collection of sediment data by manual grab methods impractical. As a result several organizations, such as Federal Interagency Sedimentation Project (FISP), and United States Geological Survey (USGS), accompanied by commercial companies, have developed and evaluated several models of automated samplers. The USGS has identified seventeen optimum criteria for Automatic Pumping-Type Samplers in USGS Open-File Report 86–531, by Edwards and Glysson (1988):

1. Isokinetic sample collection if intake is aligned with approaching flow.
2. Suspended-sediment sample should be delivered from stream to sample container without a change in sediment concentration and particle-size distribution.
3. Cross contamination of sample caused by sediment carry-over in the system between sample-collection periods should be prevented.
4. Sampler should be capable of sediment collection when concentrations approach 50,000 (mg/l) and particle diameters reach 0.250 mm.
5. Sample-container volumes should be at least 350 ml.
6. The intake tube inside diameter should be ⅜ or ¾ inch, depending upon the size of the sampler used.
7. The mean velocity within the sampler plumbing should be great enough to ensure turbulent flow (Reynolds number greater than 4000 to ensure turbulent flow).
8. The sampler should be capable of vertical pumping lifts to 35 feet from intake to sample container.
9. The sampler should be capable of collecting a reasonable number of samples, dependent upon the purpose of sample collection and the flew conditions.
10. Some provision should be made for protection against freezing, evaporation, and dust contamination.
11. The sampler-container tray unit should be constructed to facilitate removal and transport as a unit.
12. The sampling cycle should be initiated in response to a timing device or stage change.

13. The capability of recording the sample collection date and time should exist.
14. The provision for operation using DC battery power or 110-volt AC power should exist.
15. The weight of the entire sampler or any one of its principal components should not exceed 100 pounds.
16. The maximum dimensions of the entire sampler or any one of its components should not exceed 35 inches in width or 79 inches in height.
17. The required floor area for the fully assembled sampler should not exceed 9 square feet (3 ft by 3 ft).

It is essential that the an automated sampler be able to meet the majority of the outline criteria. Automated samplers generally consist of: (1) a pump to draw a suspended-sediment from the stream flow, and, in some cases, back flush to prevent cross-contamination between samples, as well as to prevent freezing during winter months; (2) a sample container unit to hold sample bottles in position for filling; (3) a sample distribution system to divert a pumped sample to the correct bottle; (4) an activation system that starts and stops the sampling cycle, typically either at a regular time interval or in response to a rise in fall of the stream (gage height); and (5) an intake system through which samples are drawn from a point in the sampled cross section.

An advantage of automated samplers over grab sampling is that automated samplers can collect suspended-sediment samples during periods of rapid stage changes caused by storm-runoff events. Automated samplers also reduce the manpower necessary to carry out intensive sediment-collection programs. However, because of their mechanical complexity, power requirements, and limited sample capacity, automated samplers often require more frequent site visits than a conventional observer station. All the automated samplers use pumps powered by batteries or an AC power supply. This presents a significant problem in remote settings, where changing or recharging batteries is difficult. Batteries also add substantial weight to a sampler unit. Moreover, these units can be prone to freezing during cold weather.

Most automated samplers need a separate flow meter to correlate sampling to the test site's flow, in order to provide flow proportional sampling. These systems are complicated and often require on-site calibration to ensure accuracy.

Sampling frequency for automatic sampling systems should be much greater at peak flows than during gradual base flows. High flows, such as those caused by a storm or spring runoff, typically contain high sediment concentrations. The peak sediment concentrations however do not usually coincide with the water-discharge peak. Therefore, a need for intermittent flow-proportional sampling is necessary to accurately depict the conditions within the steam environment.

Some of the automatic pump-type samplers are the U.S. PS-69, U.S. CS-fl, U.S. PS-82, Manning S-4050, and ISCO 1680. The U.S. PS-82 is the most recent design available from F.I.S.P. The Manning and ISCO samplers, frequently used by federal and state agencies, were developed by private companies. None of the current samplers meet all 17 of the optimum criteria set out above. The most critical of the shortcomings is that none of the samplers provide direct, proportional flow, or isokinetic, collection of samples. Examples of some sampler designs may be seen in U.S. Pat. No. 5,693,894, invented by Jobson (1997), and a technology intensive and costly sampler developed by Hungerford and Dickinson (1994), U.S. Pat. No. 5,299,141.

SUMMARY OF THE INVENTION

Therefore, one of the objects of this invention is to provide a sample collection device that takes flow proportional samples. Another object is to provide a sample pump that does not require battery or AC power. Another object is provide a flow velocity meter. Another object is provide constant pumping, in order to avoid freezing during cold weather. Another object is provide a light-weight, stand-alone sampler that is easy to manufacture. Another object is to provide a sampler that meets a majority of the USGS criteria.

The present invention meets these objects by providing a flow driven pump that uses the flow of the test site, such as a stream, to drive a pump, thereby eliminating the need for outside power for the pump. Because the pump is flow driven, it can run constantly, thereby inhibiting freezing and providing all weather suitability. The constant action of the pump also flushes the system, thereby preventing cross-contamination of samples taken at different times. The invention also incorporates a simple pulse counter that monitor's the revolutions of the turbine propeller and can be used to measure velocity. The invention also provides a collection and distribution unit that can collect and store numerous samples in a small, light-weight container. Because the pump does not require battery power, the present invention can be left in the field for extended periods of time without maintenance.

DESCRIPTION OF THE INVENTION

Figure 1:
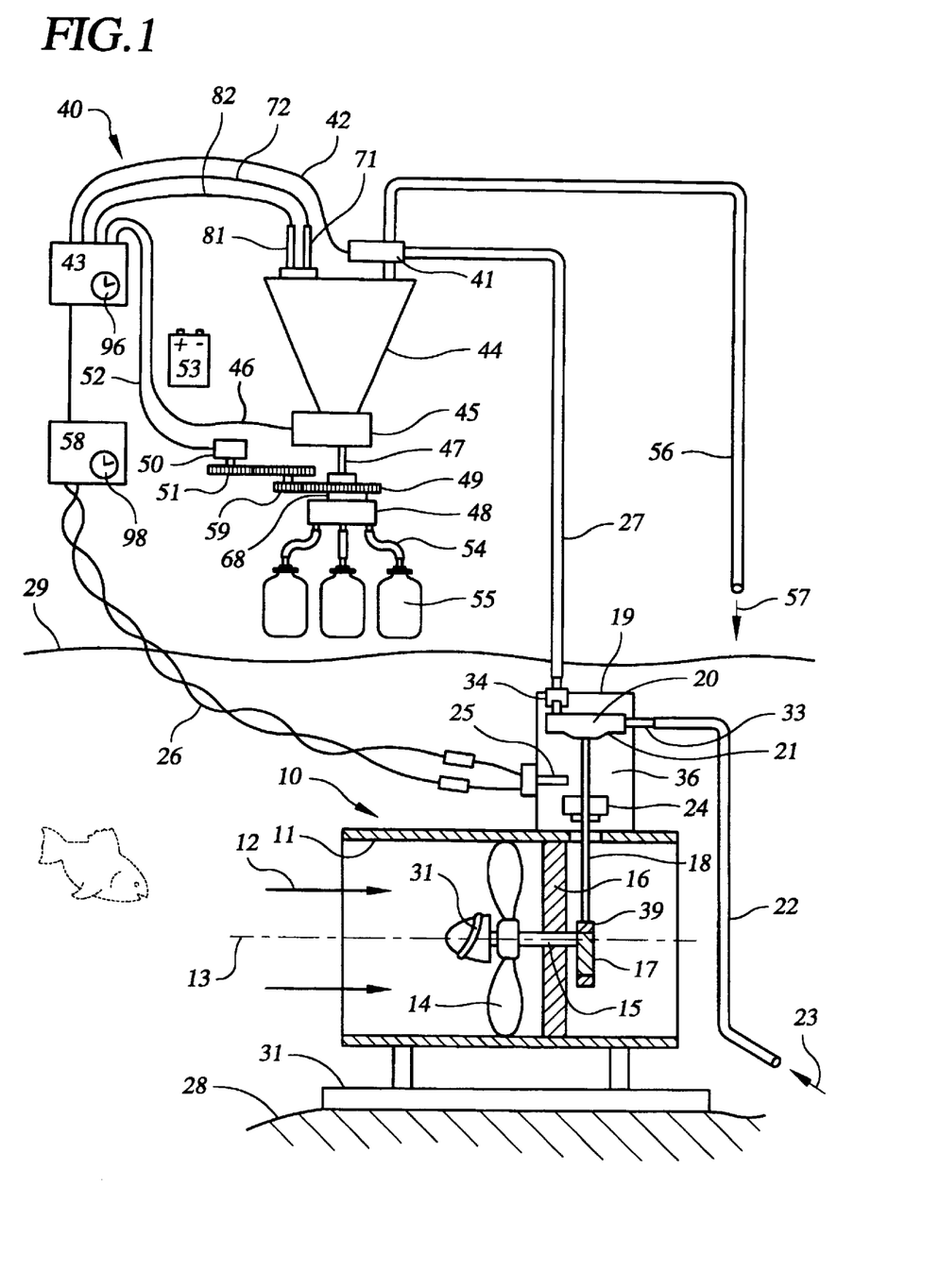
FIG. 1 is a general, overall view of the components of the present invention, and a cross-section side view of the propeller turbine and pump unit.

FIG. 1 shows an overview of one embodiment of the present invention used to take samples from a stream 29. The turbine is shown generally at 10, secured above a streambed 28 by a support bracket 31. The flow of the stream is indicated by arrows 12. The flow 12 enters a cylindrical turbine housing 11. The axis of the turbine housing 11 is indicated at 13. A vertical cross member 16 in the housing 11 supports a shaft 15 which is aligned with and rotates on the axis 13. A turbine propeller 14 is mounted to one end of the shaft 15. At the other end of the shaft is an eccentric or wobble-cam 17. As seen most clearly in FIG. 2, a connecting rod or push rod 18 has a big end 39 that rides about the wobble cam 17. The push rod 18 extends up through the housing 11 and attaches to a diaphragm 21 which is part of a conventional diaphragm pump 19. The suction of the pump 19 draws water up from the stream 29 through an inlet pipe 22, as indicated by arrow 23, and into the pump chamber 20 through inlet 33. Water is pumped out of the pump chamber 20 through outlet 34 and up outlet pipe 27.

For sampling in flowing streams, the opening of the inlet pipe 22 is ideally placed in a stable cross section of the stream and in an area of high velocity and turbulence, in order to improve sediment distribution by mixing. Ideally, the intake should be located away from a bank and oriented ninety degrees, or normal, to the stream's flow.

It can be seen that the stream's flow 12 turns the turbine propeller 14, which in turn causes the push rod 18 to actuate the pump 19. The pump 19 draws water in (23) from the stream and pumps it out through a pipe 27 for collection as a sample. It will be appreciated that the speed of the turbine 10 depends on the speed of the water flow 12 in the stream 29, and that, in turn, the speed of the pump 19 is determined by the speed of the turbine 10. Thus, if during a dry period the stream's flow 12 is slow, then sample water 23 will be pumped at a slow rate. Or, if during a period of heavy rain the stream's flow 12 is fast, then samples will pumped at a faster rate. In this way, the pumping rate is kept proportional to the stream's flow rate, thereby providing proportional sampling under different conditions. It will also be appreciated that the pump 19 does not require any external power, but is powered by the stream's flow 12, via the turbine 10.

The embodiment described above and shown in FIG. 1 uses a single turbine propeller 14 with two blades, but many conventional turbine configurations will work, such as the Pelton Wheel, Francis Turbine, and Kaplan Turbine (none shown). The Pelton Wheel and Francis Turbine require a high flow rate, which does not work well for environmental samplers in rivers or streams where flow rates may be very low. The Kaplan Turbine, a propeller turbine with variable pitch vanes, would provide the greatest efficiency over the widest range of flow rates, but the complexity of controlling the pitch of the vanes makes it a less desirable option than that shown in FIG. 1. It will also be appreciated by those skilled in the art that the size of the turbine will affect the performance of the sampler. A larger turbine 10 will provide more power to the pump 19. This is especially important in low flow rate conditions, such as a slow moving stream, where a small turbine may not be able to generate enough power to drive the pump. The propeller 14 shown in FIGS. 1 and 2 has two blades, but it is possible to use one or any number of blades. One option to increase turbine efficiency is to use more than one turbine propeller 14. Thus in an alternate embodiment, a second propeller 31 is mounted ahead of and ninety degrees offset from the first propeller 14.

Figure 2:
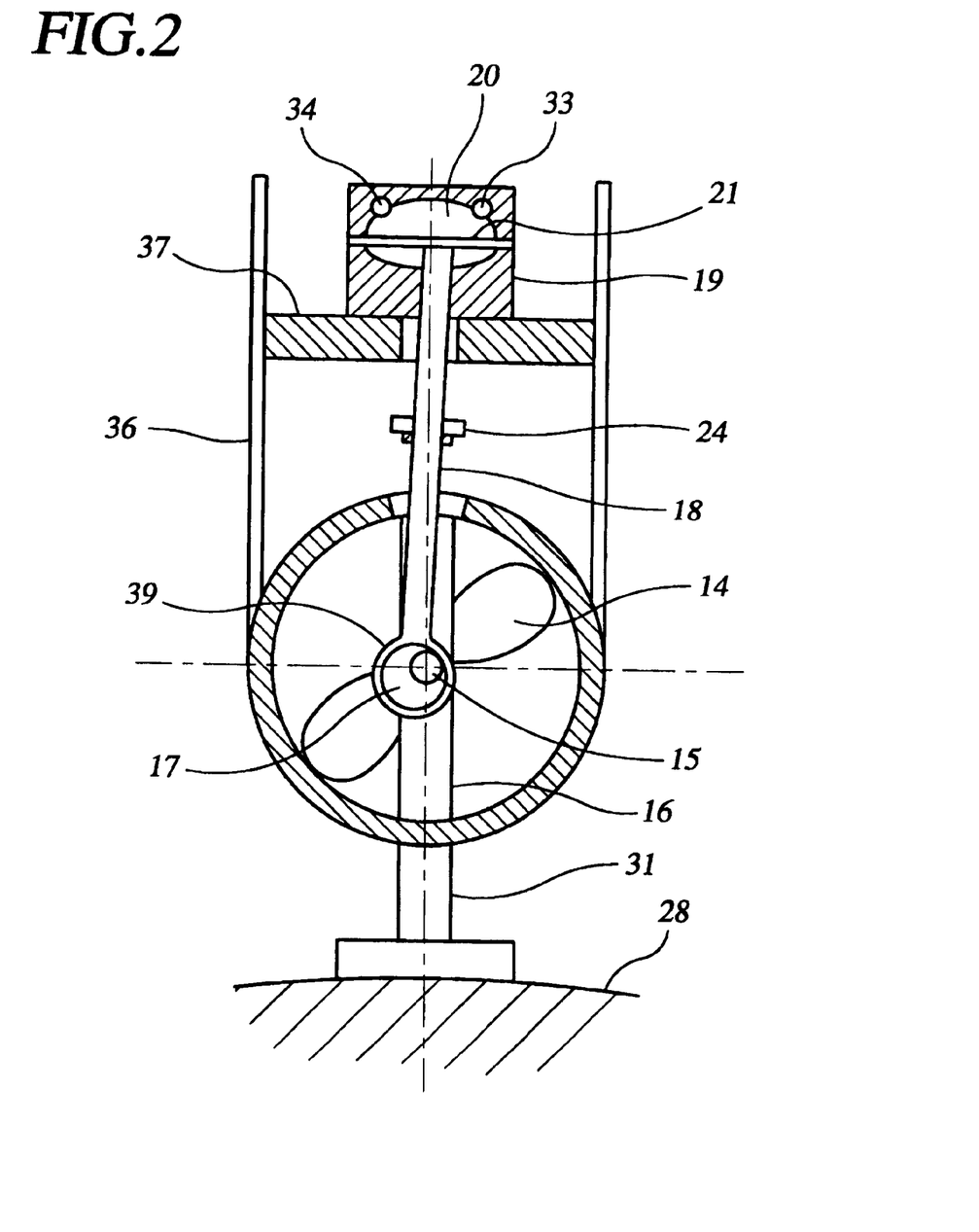
FIG. 2 is a cross-section end view of the propeller turbine and pump unit.

The pump shown in FIG. 1 is a conventional positive displacement diaphragm vacuum pump 19. This diaphragm pump has the advantage of being able to pump small volumes of fluid while requiring relatively little power to drive it. The increased efficiency of a diaphragm pump under low power make it the best pump choice for taking samples from slow moving fluids. In the embodiment shown in FIG. 1, the pump 19 is an NFT31 diaphragm pump made by KNF Neuberger. The diaphragm on this pump is self centering, eliminating the need for return springs and substantially reducing the internal resistance of the pump 19. The pump 19 uses flap valves (not shown) for the inlet 33 and outlet 33. As seen in FIG. 2, the pump 19 is mounted on a cross-member 37 which is supported above the turbine housing 11 by brackets 36. The location of the pump inlet 33 and outlet 34 are shown in FIG. 1 for purposes of illustration, while FIG. 2 shows the actual locations.

In a preferred embodiment, a collar 24 on the push rod 18 is a magnet. When the magnet 24 is passes a reed switch 25, an electrical circuit is opened and closed. Thus, as the push rod 18 rises and falls on the wobble-cam 17, the electrical circuit is opened and closed in a cycle corresponding to one rotation of the propeller shaft 15. Wires 26 from the switch 25 are part of this electrical circuit. The wires 26 connect to a data computer 58 that monitors the opening and closing of the circuit. The data computer 58 counts the number of cycles or pulses. Since the pumping capacity of the pump 19 is known, it is possible to calculate the volume of water being pumped with each pulse. Using this information, it is possible to keep track of and control the amount of water being pumped. Data computer 58 also has an internal clock 104 and can compare the pulses to time. Empirical evidence can correlate the speed of the propeller 14 to the amount of water passing by it. Thus, using this empirical data and the pulse count, the data computer 58 can use its clock 104 to calculate the velocity of the water passing by the propeller 14, or stream flow speed. This information is one of the most important pieces of sampling data.

Figure 3:
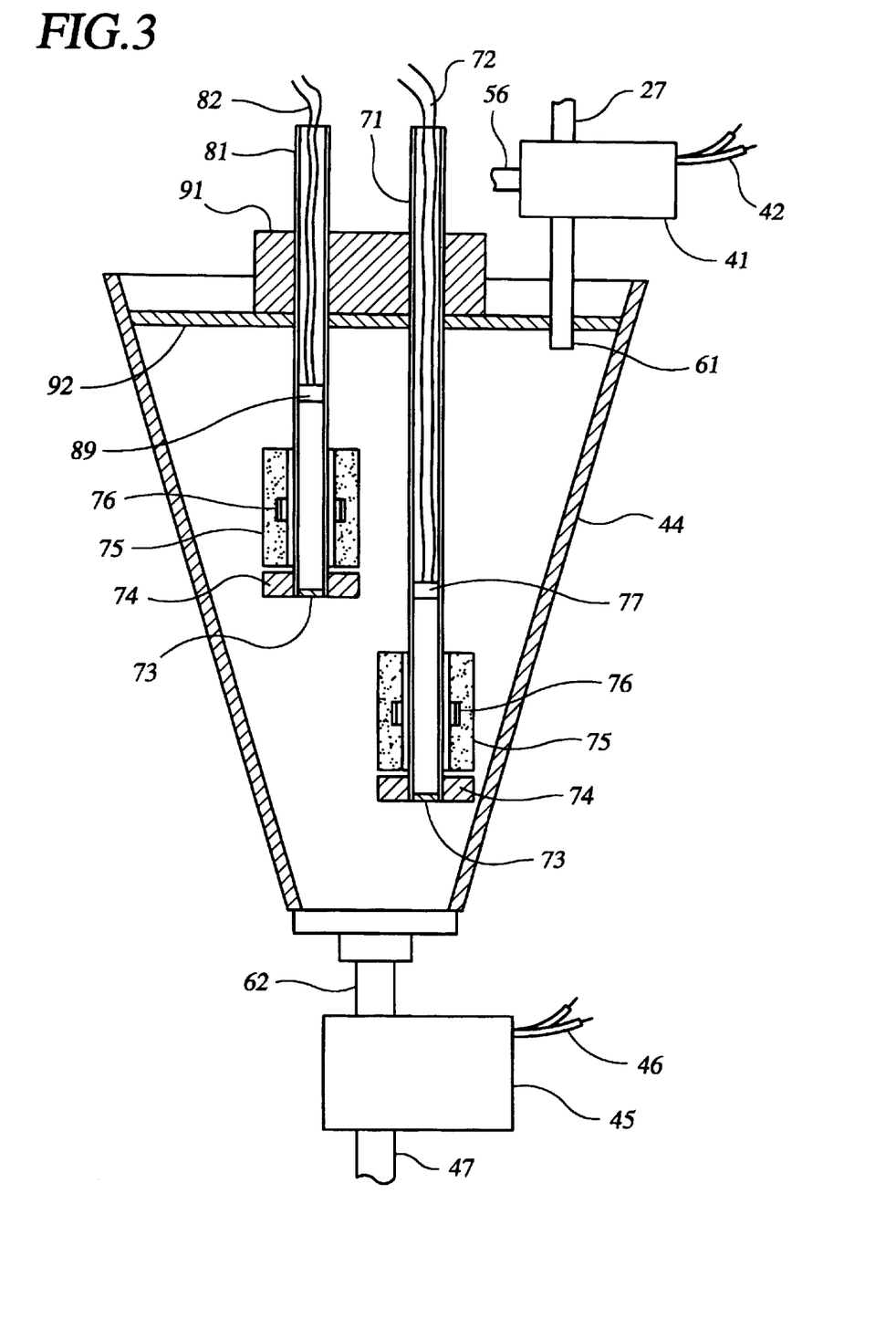
FIG. 3 is a cross-section side view of the funnel and float switches.

As seen in FIG. 3, water is pumped from pump 19, through outlet pipe 27, to solenoid switch 41. Switch 41 is a two position, three port solenoid operated switch, such as a Parker Fluid Control Valve. When no current is applied, switch 41 is idle and the three-way valve directs water out a continuous drain port 56, through a drain pipe 56, which spills the water back into the stream, as indicated by arrow 57. When a current is sent by the controller computer 43 to switch 41 through wires 42, a needle valve (not shown) is retracted by the solenoid (not shown) and water flows through funnel entry port 61 into the sample collection funnel 44. A cover 92 seals the top of the funnel 44 and protects the sample from contamination. At the bottom of funnel 44 is another solenoid switch 45. When switch 45 is idle, the valve (not shown) is open to funnel drain port 62. When a current is sent by the controller 43 to switch 45 through wires 46, the valve in the switch 45 is closed. When the sampler is ready to take a sample, controller 43 sends a current to switches 41 and 45. This current will open the valve in switch 41 and direct incoming water into the funnel 44. The controller will simultaneously send a current to switch 45, thereby closing its valve, so that water will accumulate in the funnel 44.

The amount of water in funnel 44 can be measured by counting the pulses from switch 25 and correlating that pulse count to the volume of each pump stroke. The data computer 58 can be programmed to count a pre-set number of pulses before sending a signal to the controller 43 to cut-off current to switch 45 and allow the sample collected in funnel 44 to drain out through port 47. Alternatively, one or more floats 75 can be placed in funnel 44 to monitor when the sample pumped in has reached a predetermined level. As seen in FIG. 3, a conduit 71 is held in place by a securing block 91 mounted atop the funnel cover 92. The conduit 71 extends down into the funnel 44. A cap 73 at the bottom of the conduit 71 prevents water from entering the conduit 71. A float 75 can ride freely up and down the outside of conduit 71. A C-clip or stop 73 on conduit 71 prevents the float 75 from dropping off. In float 75 are two magnets 76, balanced 180 degrees apart. As water rises in funnel 44, float 75 rises. A reed switch 77 inside conduit 71 is located at a point related to the height of water desired in the funnel 44. For example, the invention can be set to collect ten milliliters of water by adjusting the height of switch 77 in conduit 71 to correspond to that amount of water in funnel 44, at which point the magnet 76 in float 75 triggers reed switch 77. Wires 72 from switch 77 send a signal to the controller 43, and the controller stops the current to solenoid switches 41 and 45, thereby stopping the flow of water into the sample collection funnel 44 and allowing the sample to drain out of the funnel 44 through drain port 62, then through the open valve in switch 45, into drain pipe 47, and from there to the distributor 48.

Sample collection funnel 44 may designed to have very steep sides, so that sample fluids will drain completely, thereby preventing cross contamination of samples.

Figure 4:
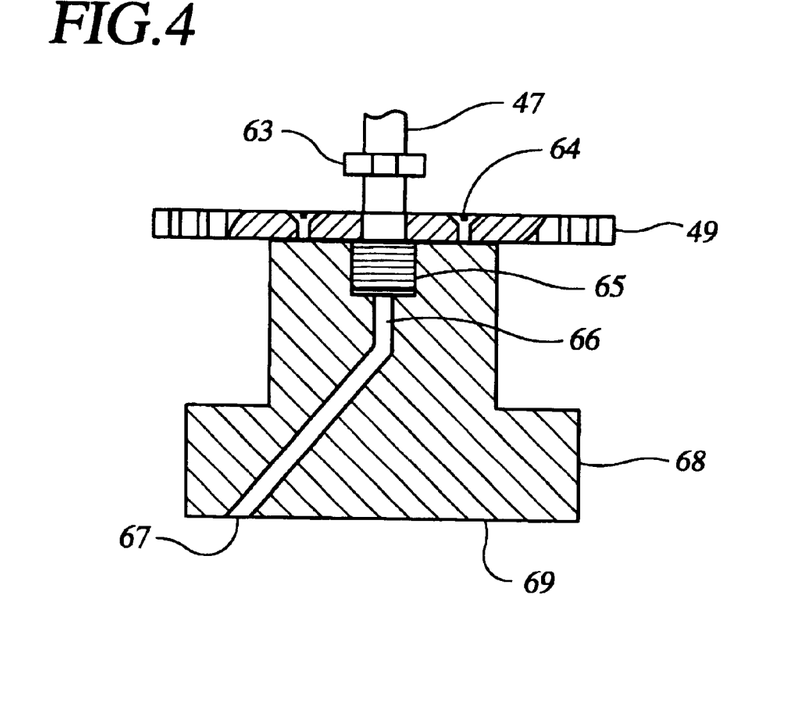
FIG. 4 is a cross-section side view of the distributor rotor.
Figure 5:
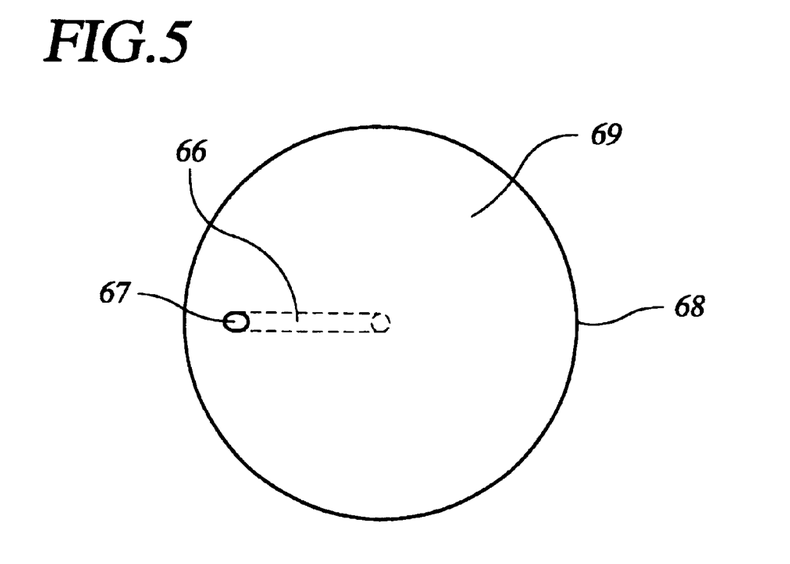
FIG. 5 is a bottom view of the distributor rotor, showing the water channel outlet.
Figure 6:
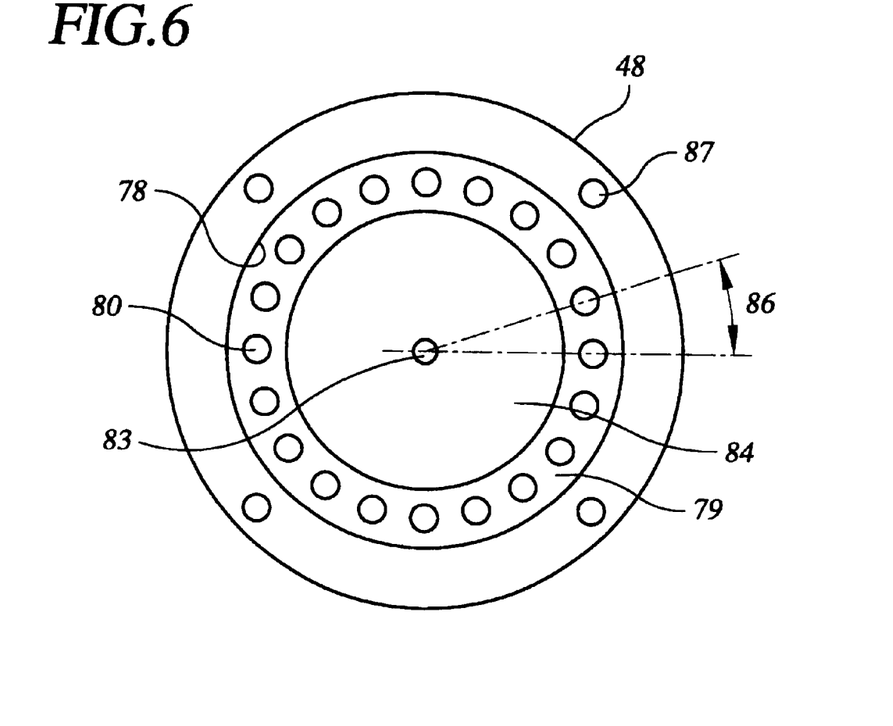
FIG. 6 is a top view of the distributor housing.
Figure 7:
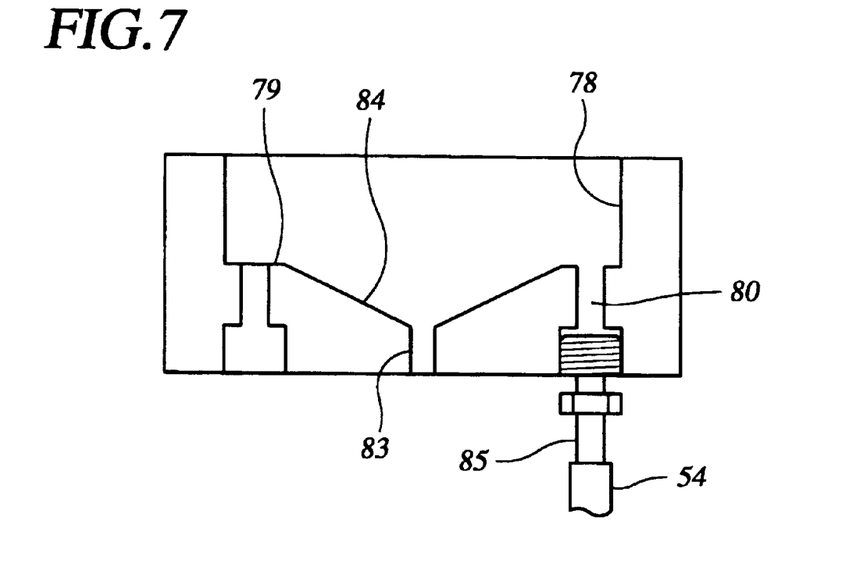
FIG. 7 is a cross-section side view of the distributor housing.

FIGS. 4 through 7 show the design of the distributor 48. The distributor body 48 is shown in FIGS. 6 and 7, and the distributor rotor 68 is shown in FIGS. 4 and 5. As shown in FIG. 4, drain pipe 47 extends down into a distributor inlet fitting 63. Fitting 63 is secured to the distributor rotor 68 at 65. Water passes through the fitting 63 into channel 66, and channel 66 directs the water out to a discharge hole 67 at the perimeter of the bottom 69 of the rotor 68. FIG. 5 shows the bottom 69 of the rotor 68 and the location of the discharge hole 67. As shown in FIGS. 6 and 7, rotor 68 rides in the recess 78 of the distributor body 48. The bottom 69 of the rotor 68 rests on a ledge 79 in recess 78. FIG. 6 shows that sixteen drain holes 80 are arranged around the perimeter of ledge 79. The holes 80 allow sample water to drain out of the distributor 48 through fittings 85 and into sample collection tubes 54. Holes 87 in the outside of the distributor body 48 are for securing the distributor to some stable platform, as shown in FIG. 9. A funnel drain 84 in distributor 48 allows any water that has leaked between the rotor 68 and the ledge 79 to drain down through drain hole 83, thereby preventing collection of leaking water and cross contamination of samples, Referring back to FIG. 4, a gear 49 is secured to the top of rotor 68 by screws 64. The rotor gear 49 meshes with a set of reduction gears 59. A conventional DC stepper motor 50 drives a gear 51, and through the set of reduction gears 59. Upon receiving current, the DC stepper motor 50 will make a single rotation, then stop. The reduction gears 59 are sized to translate the single rotation of the stepper motor 50 into an incremental movement of distributor rotor 68. This incremental rotation, shown by the angle at 86 in FIG. 6, will place the discharge hole 67 of the rotor 68 directly over one of the sixteen drain holes 80 in the distributor 48.

When the controller 43 cuts off current to the solenoid switches 41 and 45, water drains out of collection funnel 44 to distributor 48, which distributes the sample to a particular sample bottle 55. A clock 96 in controller 43 allows a pre-programmed amount of time to pass to allow the sample to drain completely from the funnel 44 and through the distributor 48. After that set time has passed, the controller sends a signal to the stepper motor 50, which causes the motor 50 to complete a single rotation and move the rotor 68 to the next distributor sample hole 80.

Figure 8:
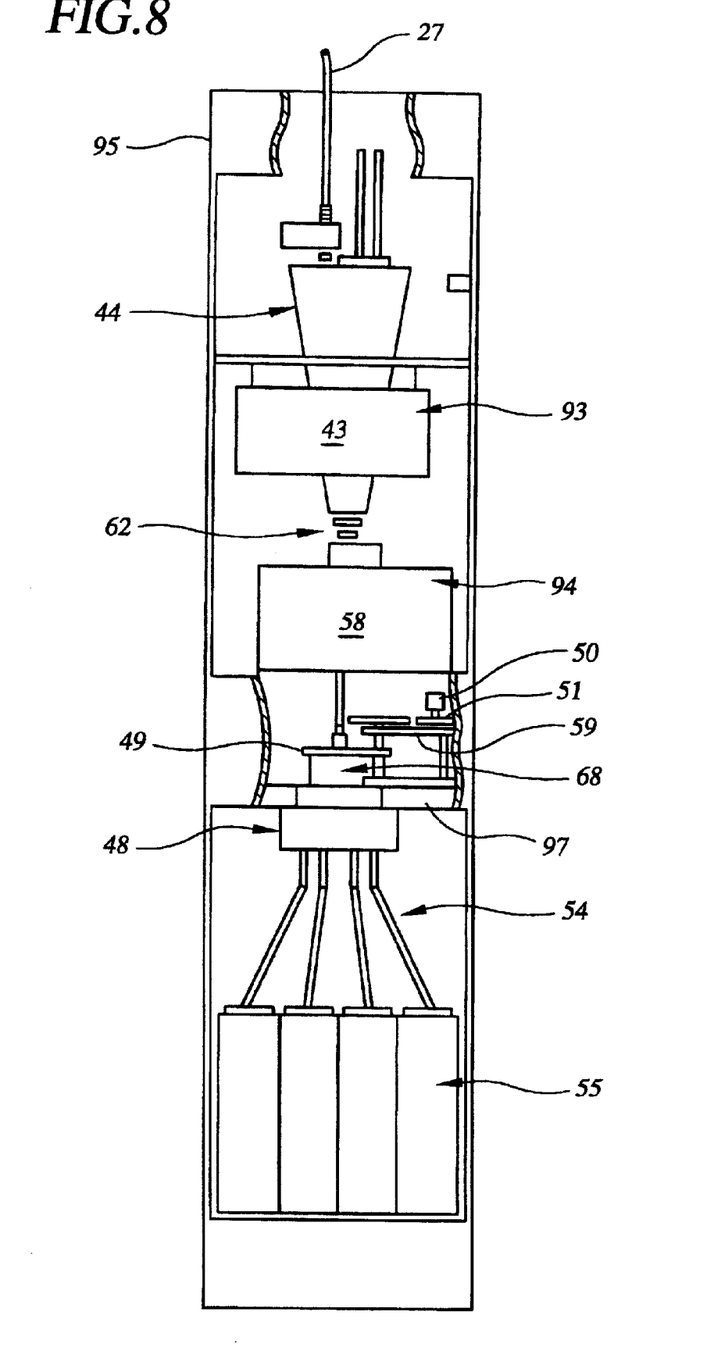
FIG. 8 is a cross-section side view of the collection and distribution unit.

FIG. 8 shows a design for a collection and distribution unit, indicated generally by 40. Such a unit facilitates transport of the sampler, especially to remote locations. All the components of the sampler, other than the turbine and pump unit 10, can be arranged in collection unit 40 so that on-site set-up only requires the attachment of a few hoses and wires. Upper and lower doors (not shown) in housing 95, open for access to the components and sample bottles 55. In the arrangement shown in FIG. 8, a cylindrical PVC housing 95 is used to hold the collection and distribution components. The sample funnel 44 is secured at the top. Sample inlet pipe 27 enters through the open top of the housing 95 and mates with solenoid switch 41. The controller computer 43 is mounted in a sealed box 93 in front of the funnel 44 (wiring is not shown in this figure). The data computer 58 is mounted in its own box 94 below the controller 43. Drain pipe 47 directs sample water to the distributor rotor 68, and the motor 50 reduction gear set 59 are mounted below the data computer 58. The battery 53 or batteries are not shown in this figure, but they may be secured around the distributer rotor 68 on the platform 97. The distributor 48 is screwed to the platform 97. The collection bottles 55 are stored in the bottom compartment of the unit 40.

Figure 9A:
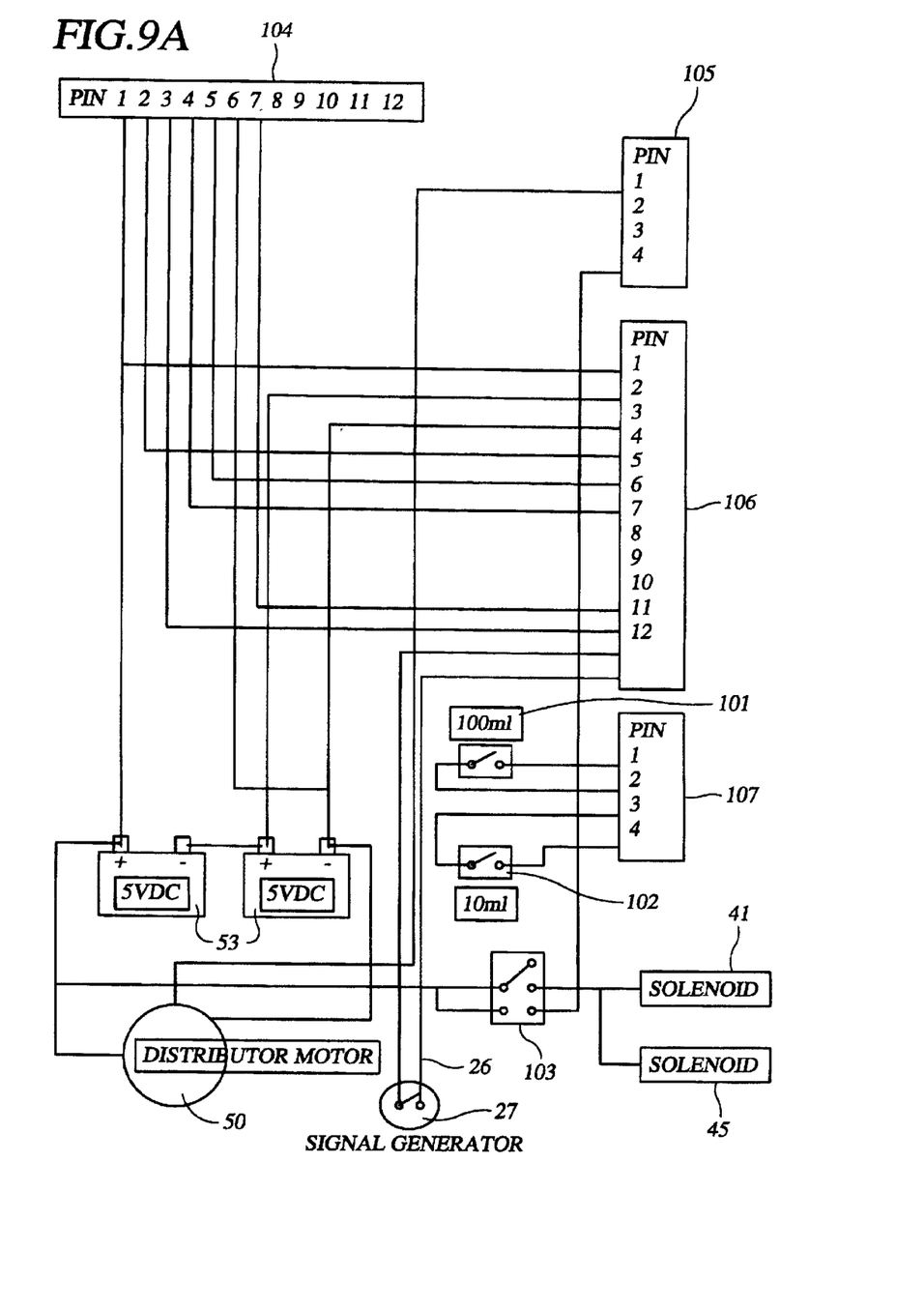
FIG. 9A is a schematic of half of the data and control circuitry.
Figure 9B:
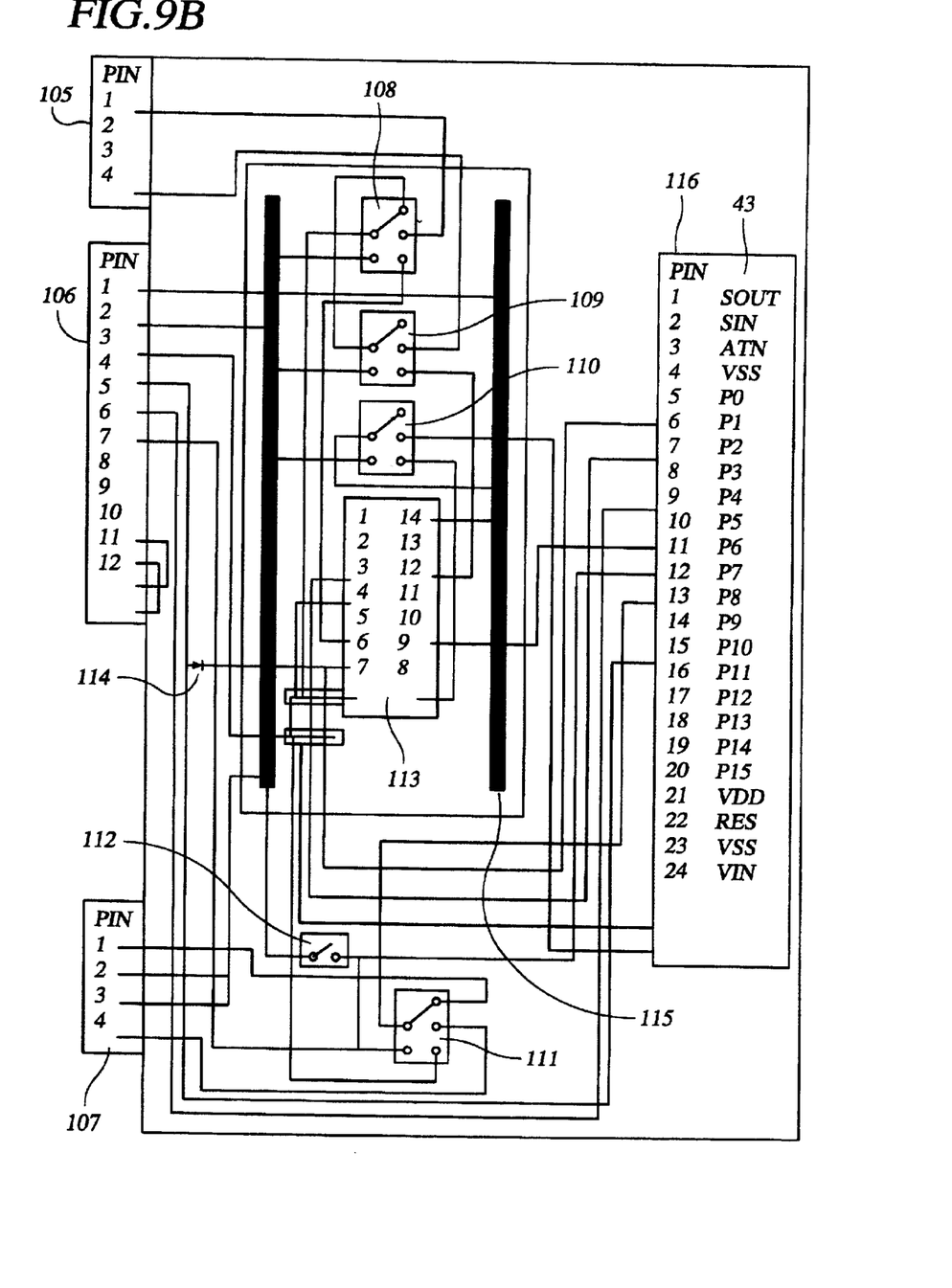
FIG. 9B is a schematic of the other half of the data and control circuitry.

FIGS. 9A and 9B show the schematic for the invention. Referring to FIG. 9A, switch 101 allows the user to select one sample volume, which is shown as 100 milliliters, and switch 102 allows the selection of a different volume, shown here, as an example, as 10 milliliters. It will be appreciated that any number of switches may be used to choose a wide variety of settings. Two six volt batteries 53 provide power to the unit. A relay 103 provides switching for the solenoid switches 41 and 45. A connector 104 plugs into the data computer 58. Any conventional single board computer, such as a CMD118A8 board produced by Axiom Manufacturing, may be used as the data computer 58. The data computer counts the pulses from the reed switch 26 on the pump 19 push rod 18. The pulses can be stored in memory and a program can be developed to take samples after a certain number of pulses have been counted. The data computer also has an internal clock 98, which can be used to order samples based upon time intervals. Moreover, the data computer 58 can calculate, store in its memory, and chart data concerning the test site's flow speed. To do this, empirical information relating the speed of the propeller 14 to the speed of water driving the propeller 14 is gathered. That empirical data is compared to the pulse signals from the reed switch 26, and the clock 98 is used to provide the test flow's velocity.

Referring to FIG. 9B, relay 108 is another switch controlling the stepper motor 50. Relay 109 is another switch controlling the solenoid switches 41 and 45. Relay 110 turns the controller 43 on when a signal is received from the data computer 58. Relay 111 selects which float, 71 or 81, the controller will use to control the amount of sample taken. Re-set switch 112 can re-boot the system if it locks-up. Relay driver 113 amplifies the voltage and current. Diode 114 prevents back-feeding of signals to the data computer. Internal buses are shown at 115. Connector 116 plugs into the controller computer 43. A conventional microprocessor, such as a Paralax Industrial Basic Stamp II, may be used. The controller 43 receives the signal from the data computer 58 to take a sample, and controls the sample taking process by sending current to solenoid switches 41 and 42, waiting a pre-set time for the sample to drain from the funnel 44 and through the distributor 48, then sending a signal to the stepper motor 50, which shifts the distributor rotor 68.

Figure 10:
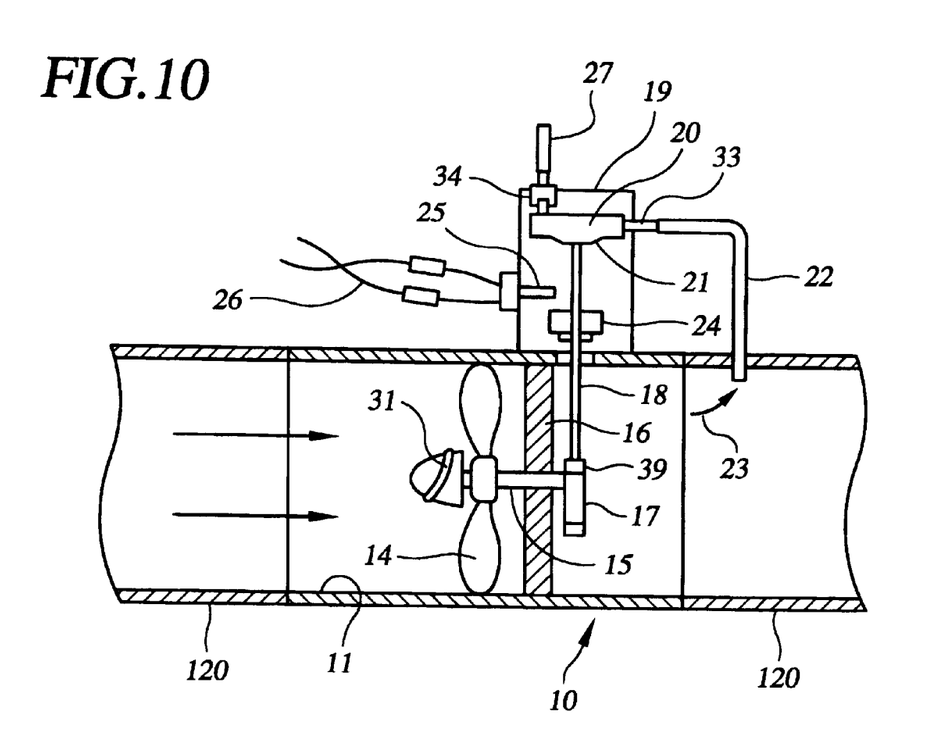
FIG. 10 is a cross-section of the turbine and pump unit inserted between sections of pipe.

It will be appreciated by those skilled in the art, that the turbine and pump unit 10 is ideally suited to many applications. The description provided above is but one embodiment set in the context of taking water samples from a stream or river. But, the invention may also be used to take samples from any moving fluid, including canals, irrigation ditches, storm drains, and sewer systems. The fluid need not be limited to water. Moreover, the present invention may also be adapted to taking samples from pipes. As shown in FIG. 10, the pump unit 19 may be attached to the turbine housing 11 and sealed to prevent fluids from escaping. The inlet pipe 22 can be directed through the turbine housing 11 to take samples from within the housing 11. In this way, the housing 11 may be inserted between sections of pipe 120 and used to pump samples.

The drawings and description set forth here represent only some embodiments of the invention. After considering these, persons skilled in the art will understand that there are many ways alternative embodiments and applications envisioned. The inventors contemplate that the use of alternative structures, which result in flow proportional sampler using the principles disclosed and the invention claimed, will be within the scope of the claims.

What we claim is:

1. A fluid sampler turbine pump unit comprising:
   a housing forming an open cylinder and having a first open end and a second open end an axis,
   an axle in the cylinder and located along the axis, wherein the axle further comprises a propeller end and an eccentric end,
   a propeller located in the cylinder and mounted on the propeller end of the axle,
   an eccentric mounted at the eccentric end of the axle, wherein the eccentric is driven directly by the axle,
   a rod having a first end and a second end,
   wherein the first end rides on and is actuated by the eccentric end, and
   a pump connected to the second end of the rod the pump having an inlet to draw fluid in and an outlet to pump fluid out.

2. The fluid sampler of claim 1 wherein the pump is a diaphragm pump.

3. The fluid sampler of claim 1, wherein the eccentric is a wobble-cam.

4. The fluid sampler of claim 1 further comprising a means to detect rotation of the axle.

5. The fluid sampler of claim 1 further comprising a magnet mounted on the rod, a switch adjacent the magnet, and an electrical circuit connected to the switch, wherein movement of the rod opens and closes the electrical circuit, thereby detecting rotation of the axle.

6. A fluid sampler comprising:
   a housing having a first open and and a second open end and an axis,
   an axle running on the axis and having an eccentric, wherein the eccentric actuates a rod, the rod having an eccentric end actuated by the eccentric and an actuation end,
   a turbine mounted on the axle, and
   a pump connected to the actuation end of the rod, the pump having an inlet to draw fluid in from a fluid source and, an outlet conduit to pump the fluid out,
   a collector to receive the fluid from the outlet conduit, and
   a valve to keep the fluid in the collector,
   a second fluid conduit connected to the collector to receive the fluid released from tho collector when the valve is opened,
   a distributor connected to the second fluid conduit to direct the fluid received from the second fluid conduit to one of a plurality of sample containers.

* * * * *